United States Patent
Almansour et al.

(10) Patent No.: US 10,590,147 B1
(45) Date of Patent: Mar. 17, 2020

(54) SPIROOXINDOLE-PYRROLOTHIAZOLE HETEROCYCLIC HYBRIDS

(71) Applicant: KING SAUD UNIVERSITY, Riyadh (SA)

(72) Inventors: Abdulrahman Ibrahim Almansour, Riyadh (SA); Suresh Kumar Raju, Riyadh (SA); Arumugam Natarajan, Riyadh (SA); Rajapandiyan Krishnamoorthy, Riyadh (SA); Ali A. Alshatwi, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/566,851

(22) Filed: Sep. 10, 2019

(51) Int. Cl.
 C07D 513/22 (2006.01)
 A61P 31/04 (2006.01)

(52) U.S. Cl.
 CPC ............ *C07D 513/22* (2013.01); *A61P 31/04* (2018.01)

(58) Field of Classification Search
 CPC .................................................. C07D 513/22
 See application file for complete search history.

(56) References Cited

U.S. PATENT DOCUMENTS

| | | | |
|---|---|---|---|
| 9,822,128 B1 | 11/2017 | Barakat et al. | |
| 10,144,739 B2 | 12/2018 | Gollner et al. | |
| 2016/0000764 A1 | 1/2016 | Weinstabl et al. | |

FOREIGN PATENT DOCUMENTS

WO 2012099453 A1 7/2012

OTHER PUBLICATIONS

Karthikeyan et al., Bioorganic & Medicinal Chemistry Letters, 20(1), Jan. 1, 2010, pp. 350-353. (Year: 2010).*

(Continued)

*Primary Examiner* — Laura L Stockton
(74) *Attorney, Agent, or Firm* — Richard C. Litman; Nath, Goldberg & Meyer

(57) ABSTRACT

The spirooxindole-pyrrolothiazole heterocyclic hybrids are compounds having the formula:

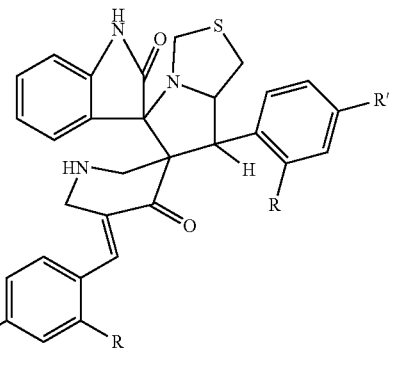

6a, R = H, R' = F
6b, R = F, R' = H wherein R is hydrogen and R' is fluorine (compound 6a) or R is fluorine and R' is hydrogen (compound 6b). The hybrids may be obtained using a chemical synthesis process involving 1,3-dipolar cycloaddition of 3,5-bis(4/2-fluoro-benzylidene) piperidin-4-ones with isatin and 4-thiazolidinecarboxylic acid in a suitable solvent, preferably 1-butyl-3-methyl-imidazolium bromide ("[bmim]Br"), and preferably under microwave irradiation. Both of these new hybrids demonstrate antimicrobial activity against both gram positive and gram negative drug resistant and non-resistant bacterial pathogens, although compound 6a exhibits more potent antibacterial activity than compound 6b.

18 Claims, 10 Drawing Sheets

(56) References Cited

OTHER PUBLICATIONS

Lotfy et al., Bioorganic & Medicinal Chemistry, 25(4), Feb. 15, 2017, pp. 1514-1523. (Year: 2017).*
Karthikeyan et al., "A highly atom econimic, chemo-, regio- and stereoselective synthesis and evaluation of spiro-pyrrolothiazoles as antitubercular agents", Bioorganic &medicinal chemistry letters (2010), vol. 20, No. 1, pp. 350-353 (Abstract only).
"Antitubercular activity against Mycobacterium tuberculosis". PubChem AID 454541 (2010), 4 pages.
"Antitubercular activity against multidrug-resistant Mycobacterium tuberculosis", PubChem AID 454542 (2010), 4 pages.
"CHEMBL604285", PubChem SID: 103721852 (2010), 3 pages.
"CHEMBL610479", PubChem SID: 103721936 (2010), 3 pages.
Li et al., "Combinatorial Synthesis of Functionalized Spirooxindole-Pyrrolidine/Pyrrolothiazole Derivatives via Three-Component 1,3-Dipolar Cycloaddition Reactions", ACS Comb. Sci. (2014) vol. 16, pp. 506-512.
Paneri et al., "A straightforward Microwave assisted green synthesis of Functionalized Spirooxindole-Pyrrolothiazole Derivatives via Three-Component 1,3-Dipolar Cycloaddition Reactions", Chemistry & Biology Interface (2016), vol. 6, No. 4, pp. 224-233.
Lotfy et al., "Synthesis of new spirooxindole-pyrrolothiazole derivatives: Anti-cancer activity and molecular docking", Bioorganic & Medicinal Chemistry (2017), vol. 25, Iss. 4, pp. 1514-1523 (Abstract only).

* cited by examiner

Strychnofoline

Rhynchophylline

Alstonisine

Spirotryprostatin A

SPIROOXINDOLE-PYRROLOTHIAZOLE HETEROCYCLIC HYBRIDS

BACKGROUND

1. Field

The disclosure of the present patent application relates to heterocyclic compounds exhibiting antibacterial activity, and particularly to a pair of spirooxindole-pyrrolothiazole heterocyclic hybrids that are obtained by a synthetic process including 1,3-dipolar cycloaddition of 3,5-bis(4/2-fluorobenzylidene)piperidin-4-ones with isatin and 4-thiazolidinecarboxylic acid in 1-butyl-3-methylimidazolium bromide ("[bmim]Br") under microwave irradiation. The hybrids exhibit broad spectrum antibacterial activity.

2. Description of the Related Art

Antibiotic resistant microbes cause millions of deaths worldwide, annually. Widespread and increasing drug resistance limits the efficacy of current existing antibiotics, which exacerbates the frequency and severity of infections that lead to treatment failure. In particular, for example, the high virulence and drug resistance in humans of *Pseudomonas aeruginosa*, *Salmonella typhi* (Gram negative—G$^-$ve) and *Staphylococcus aureus* (Gram positive—G$^+$ve) have resulted in these pathogens being considered to be life-threatening bacterial pathogens that may cause sepsis and endocarditis. As a result, the discovery and development of novel antimicrobial agents with a wide range of activity against both G$^+$ve and G$^-$ve drug-resistant bacterial pathogens is desirable. Alanine racemase and sortase are unique enzymes involved in the synthesis and assembly of peptidoglycan in the cell walls of numerous G$^+$ve and G$^-$ve bacteria. Spirooxindole-pyrrolothiazole heterocyclic hybrid antimicrobials that attack bacteria through these cell wall-synthesizing enzymes have been developed. The chemical architecture of spirooxindole-pyrrolothiazole heterocyclic hybrids is not similar to existing antibiotics. Such antimicrobial compounds can be used for various applications in clinical and veterinary medicine, as well as for preservation of food and dairy products.

One efficient method for preparing heterocyclic compounds in a highly regio- and stereoselective fashion is to employ a manufacturing process using 1,3-dipolar cycloadditions, which provide complex spiro- and cyclic structures from relatively simple precursors. In particular, the chemistry of 1,3-dipolar cycloaddition of nonstabilized azomethine ylides to olefinic dipolarophiles having an exocyclic bond has gained significance in recent years, and serves as a facile route for synthesis of many spiroheterocyclic compounds comprising five-membered nitrogen heterocycles that constitute the central skeleton of numerous natural products.

Spiro compounds represent an important class of naturally occurring substances. These compounds, possessing cyclic structural backbones fused at a central carbon, are of paramount interest due to their remarkable conformational features and their structural effects on biological systems. Many natural products include heterocyclic spirooxindole hybrids, such as strychnofoline, rynchophylline, alstonisine, and spirotryprostatin A, the structures of which are depicted in FIGS. 1A to 1D, respectively. Their usefulness in medicine and therapeutics makes similar compounds attractive as synthetic targets.

The 1,3-dipolar cycloaddition of thiazolium ylides to alkenes produces pyrrolothiazole rings, which possess interesting pharmacological properties. These compounds have demonstrated a wide variety of medicinal activity, including antineoplastic, antibiotic, antidiabetic, anticonvulsant, anti-inflammatory, antileukemic, and hypoglycemic effects, as well as acting as modulators of dopaminergic neurotransmission in the central nervous system; as γ-lactam analogues of penems; and in treating Alzheimer disease. The piperidine structural moiety is associated with a wide array of biological applications, and the spiropiperidine nucleus is found in several natural alkaloids possessing high agonistic activity and selectivity, such as Ro64-6198, and demonstrating anxiolytic properties. Further, substituted piperidines are key building blocks for the synthesis of various alkaloids and pharmaceutically important drug molecules. Therefore, a method for synthesis of a single molecular framework that integrates piperidinone and pyrrolothiazole rings bonded through a spiro carbon provides a great platform for determining and producing potentially beneficial compounds.

Thus, spirooxindole-pyrrolothiazole heterocyclic hybrids solving the aforementioned problems are desired.

SUMMARY

The spirooxindole-pyrrolothiazole heterocyclic hybrids are compounds having the formula:

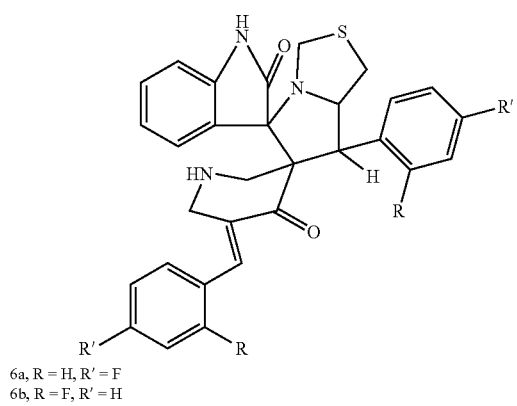

6a, R = H, R' = F
6b, R = F, R' = H wherein R is hydrogen and R' is fluorine (compound 6a) or R is fluorine and R' is hydrogen (compound 6b). The hybrids may be obtained using a chemical synthesis process involving 1,3-dipolar cycloaddition of 3,5-bis(4/2-fluoro-benzylidene) piperidin-4-ones with isatin and 4-thiazolidinecarboxylic acid in a suitable solvent, preferably 1-butyl-3-methyl-imidazolium bromide ("[bmim]Br"), and preferably under microwave irradiation. This greener approach provides a method of producing the resulting dispiro heterocyclic hybrids in a single step, providing good yield and a shorter reaction time compared to conventional methods used previously to produce similar heterocyclic hybrids. Both of these new hybrids demonstrate antimicrobial activity against both gram positive and gram negative drug resistant and non-resistant bacterial pathogens, although compound 6a exhibits more potent antibacterial activity than compound 6b.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
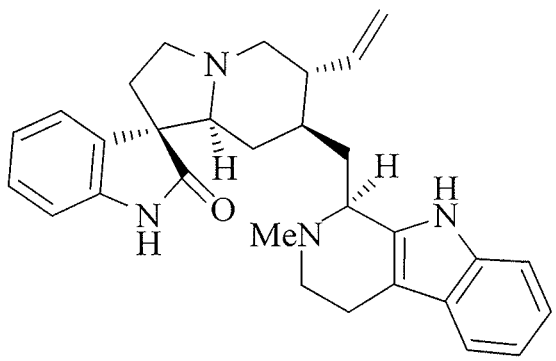
FIG. 1A is the structural formula of strychnofoline, a spirooxindole heterocyclic hybrid of the prior art.
Figure 1B:
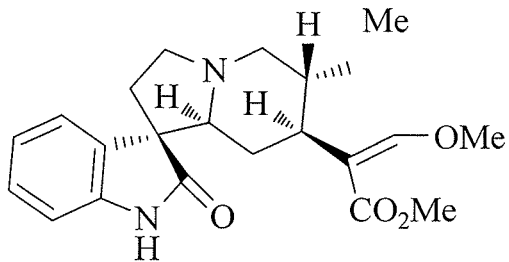
FIG. 1B is the structural formula of rynchophylline. a spirooxindole heterocyclic hybrid of the prior art.
Figure 1C:
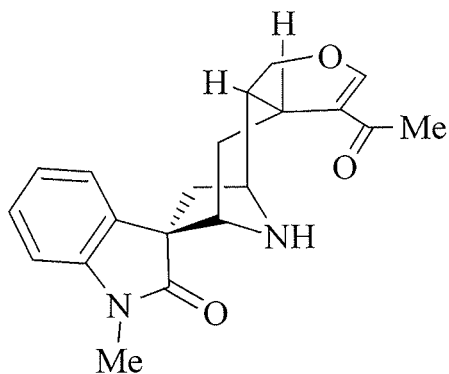
FIG. 1C is the structural formula of alstonisine, a spirooxindole heterocyclic hybrid of the prior art
Figure 1D:
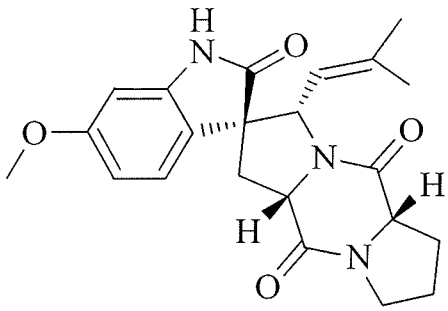
FIG. 1D is the structural formula of spirotryprostatin A, a spirooxindole heterocyclic hybrid of the prior art.

The spirooxindole-pyrrolothiazole heterocyclic hybrids are compounds having the formula:

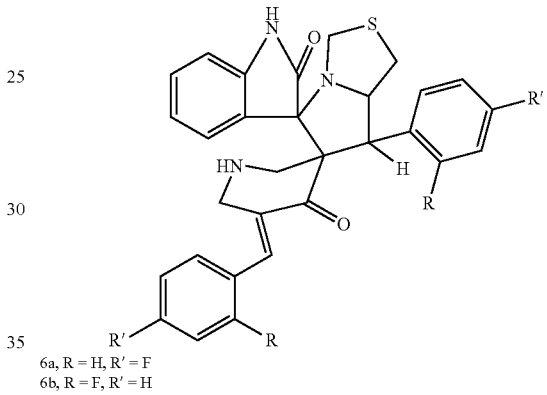

6a, R = H, R' = F
6b, R = F, R' = H wherein R is hydrogen and R' is fluorine (compound 6a) or R is fluorine and R' is hydrogen (compound 6b). The hybrids may be obtained using a chemical synthesis process involving 1,3-dipolar cycloaddition of 3,5-bis(4/2-fluoro-benzylidene) piperidin-4-ones with isatin and 4-thiazolidinecarboxylic acid in a suitable solvent, preferably 1-butyl-3-methyl-imidazolium bromide ("[bmim]Br"), and preferably under microwave irradiation. This greener approach provides a method of producing the resulting dispiro heterocyclic hybrids in a single step, providing good yield and a shorter reaction time compared to conventional methods used previously to produce similar heterocyclic hybrids. Both of these new hybrids demonstrate antimicrobial activity against both gram positive and gram negative drug resistant and non-resistant bacterial pathogens, although compound 6a exhibits more potent antibacterial activity than compound 6b.

Figure 2:
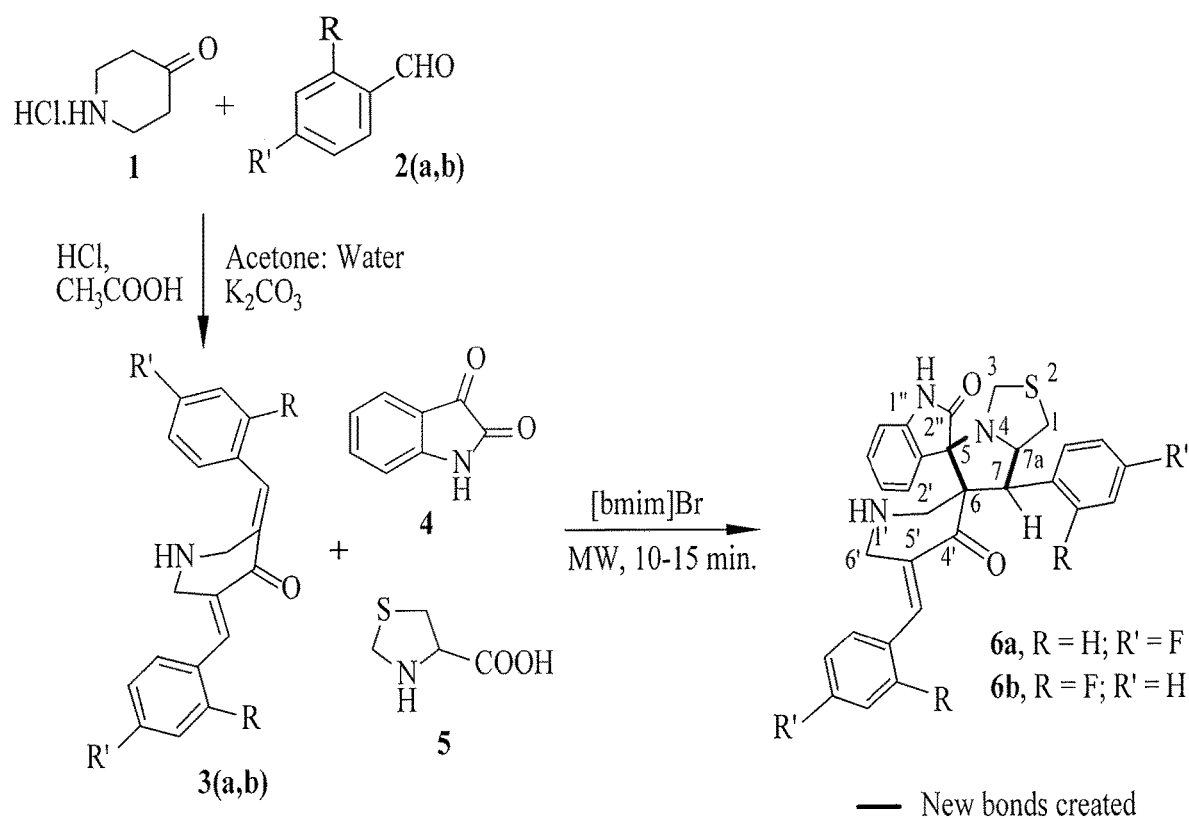
FIG. 2 is a reaction scheme for the synthesis of the spirooxindole-pyrrolothiazole heterocyclic hybrids 6a and 6b.

The dispirooxindole-pyrrolothiazole heterocyclic hybrids 6a, 6b were synthesized as outlined in FIG. 2. The syntheses of dipolarophile 3,5-bis(4/2-fluorobenzylidene)piperidin-4-ones 3a, 3b were performed following the procedure involving the reaction of aldehyde 2a (R═H and R'═F) or 2b (R═F and R'═H) (2 mmol) with 4-piperidone hydrochloride monohydrate 1 (1 mmol) in acetic acid.

The three component 1,3-dipolar cycloaddition of 3,5-bis (4/2-fluorobenzylidene) piperidin-4-ones 3a, 3b with azomethine ylide generated in situ from isatin 4 and 4-thiazolidine-carboxylic acid 5 in [bmim]Br produced the spiro [5.3"]-oxindole-spiro-[6.2']-6'-(fluorophenyl-methylidene)

tetrahydro-4'(1H)-pyridinone-7-(fluorophenyl)tetrahydro-1H-pyrrolo[1,2-c][1,3] thiazoles 6a, 6b in excellent yield. See FIG. 2.

Initially, reaction optimization for this 1,3-dipolar cycloaddition reaction was investigated by reacting an equimolar mixture of 3,5-bis[(E)-4-fluorophenylmethylidene]-tetrahydro-4(1H)-pyridinone (3a), isatin and 4-thiazolidinecarboxylic acid in methanol at reflux for 1 hour, which produced the dispirooxindole-pyrrolothiazole 6a at a 60% yield. The same reaction was also carried out in dioxane, methanol:dioxane (1:1), ethanol, and isopropanol, respectively, producing the cycloadduct in 58%, 60%, 62% and 65% yields, respectively.

In order to consider whether a more-polar environment could accelerate the reaction, we tried the reaction in an ionic liquid—[bmim]Br. An equimolar mixture of the reactants in [bmim]Br (200 mg) in an oil-bath was stirred at 100° C. for 30 minutes. After completion of the reaction, as evidenced by thin layer chromatography (TLC), the product was isolated and purified through column chromatography. As expected, the spiro cycloadduct formed rapidly and in an excellent yield (89%). Accordingly, [bmim]Br was chosen as the suitable reaction medium for these dipolar cycloaddition reactions.

In order to further reduce the reaction time, the same reaction was also performed under microwave irradiation, since reactions under microwave irradiation are known to occur faster than with conventional methods. As expected, the reaction was completed even faster—in 10 minutes. The optimal reaction condition thus established was then used for the synthesis of the other cycloadduct 6b. See FIG. 2. The ionic liquid is recovered and reused, and its efficacy is significantly undiminished in subsequent use.

The various reaction reagents, reaction times and conditions, and yields are listed in Table 1.

TABLE 1

Reaction optimization

| Entry | Reaction condition | Yield of 6a (%)[a] |
|---|---|---|
| 1 | Methanol, Reflux 1 h | 60 |
| 2 | Dioxane, Reflux 1 h | 58 |
| 3 | Methanol:Dioxane, Reflux 1 h | 60 |
| 4 | Ethanol, Reflux 1 h | 62 |
| 5 | Isopropanol, Reflux 1 h | 65 |
| 6 | [bmim]Br, 100° C., 30 min | 89 |
| 7 | [bmim]Br, MWI, 100° C., 10 min | 90 |

[a]Isolated yield

Structural examination of the spirooxindole-pyrrolothiazole heterocyclic hybrids 6a, 6b was accomplished using IR and NMR spectroscopic data. As an example, the IR and NMR spectral data of 6a is discussed.

The main infrared absorption peaks at $\upsilon_m$a 3397, 1708 and 1600 cm$^{-1}$ are associated with N—H, C=O and C=C respectively. In the $^1$H NMR spectrum, the H-7 proton appears as a doublet at 4.40 ppm (J=10.2 Hz), while its coupling partner, H-7a, appears as a multiplet at 4.60-4.67 ppm. The doublet of doublets at 2.80 ppm (J=10.2, 6.3 Hz) and 3.00 (J=10.2, 5.7 Hz) are attributed to 1-CH$_2$ protons, whereas 3-CH$_2$ protons furnished two doublets at 3.49 (J=7.2 Hz) ppm and 3.70 (J=7.2 Hz) ppm. The 5-CH$_2$ protons of the piperidone ring appears as a doublet integrating as one hydrogen at 3.63 ppm (J=14.1 Hz), and one hydrogen pair of doublets at 3.39 ppm (J=14.1, 2.1 Hz). The remaining two doublets at 2.30 ppm (J=12.9 Hz) and 3.90 ppm (J=12.0 Hz) are ascribable to 3'-CH$_2$ protons. The arylmethylidene proton H-8 appears as a singlet at 6.51 ppm. The singlet at 8.27 ppm is due to the NH of the oxindole ring, and the aromatic protons appear as doublets and multiplets at 6.67-7.45 ppm. The C=O of the oxindole and piperidone rings were observed at 179.1 ppm and 198.7 ppm, respectively. The $^1$H and $^{13}$C chemical shifts of the other heterocyclic hybrid 6b were also similarly characterized.

Figure 3A:
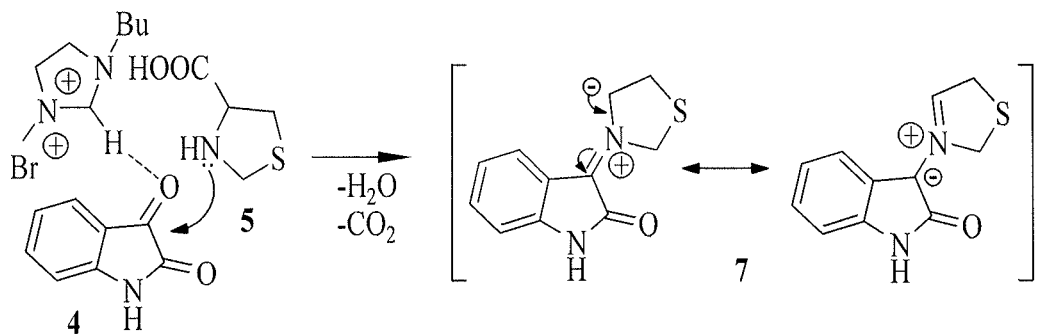
FIG. 3A is a reaction mechanism for the reaction of isatin 4 with 4-thiazolidinecarboxylic acid 5 to produce azomethine ylide 7.
Figure 3B:
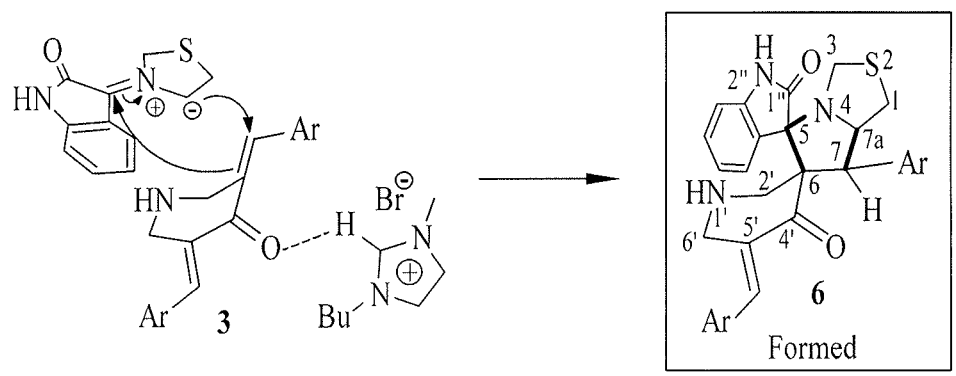
FIG. 3B is a reaction mechanism for the alternate hydrogen bond formulation between the imidazole ring hydrogen of [bmim]+(from [bmim]Br) and the carbonyl of dipolarophiles 3 to provide the addition of azomethine ylide to the (3 carbon of 3, producing the cycloadduct 6.
Figure 3C:
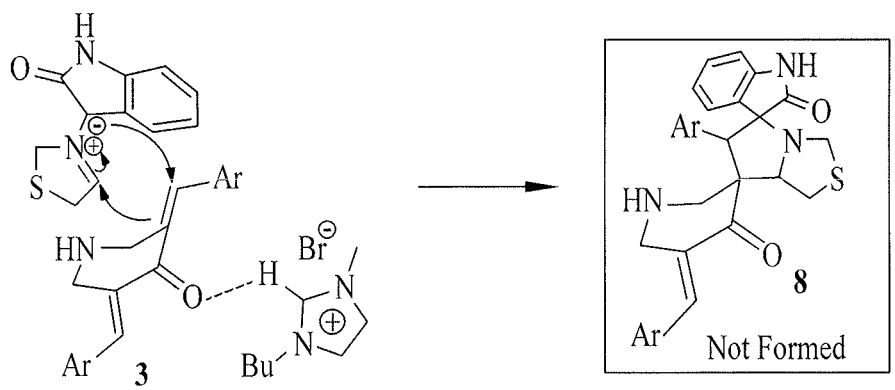
FIG. 3C is a possible reaction mechanism for alternate addition to the α carbon of 3, which would produce compound 8 except that alternate addition generally does not occur.
Figures 4A, 4B:
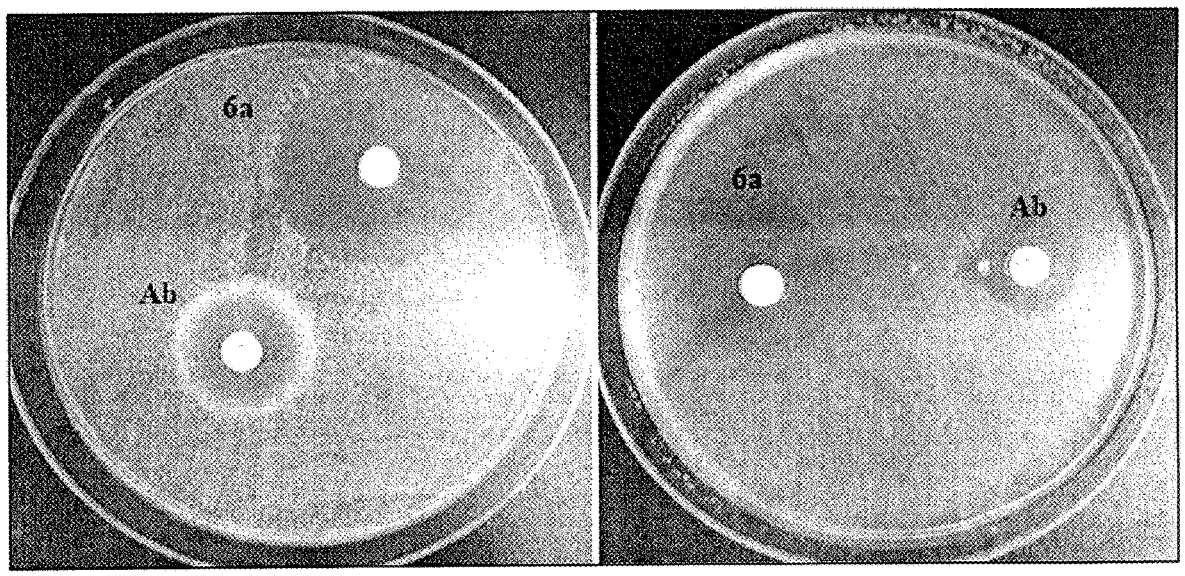
FIG. 4A is a photograph of a petri dish, demonstrating the comparative antibacterial activity of compound 6a compared to antibiotic Amoxicillin against gram positive bacterial pathogen S. epidermis.
FIG. 4B is a photograph of a petri dish, demonstrating the comparative antibacterial activity of compound 6a compared to antibiotic Amoxicillin against gram positive bacterial pathogen S. aureus.
Figures 5A, 5B:
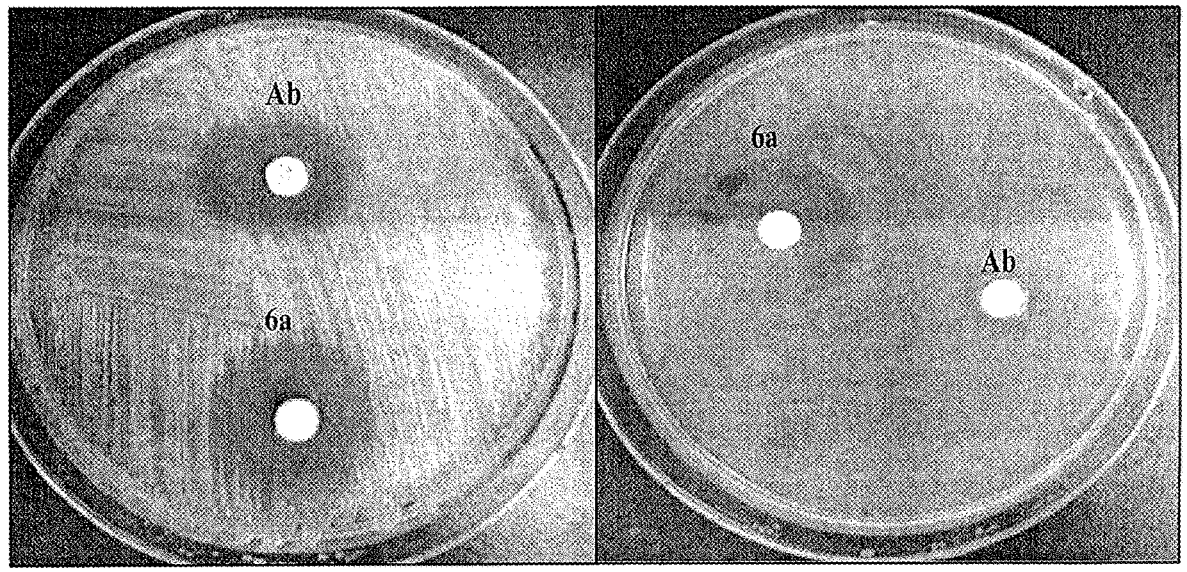
FIG. 5A is a photograph of a petri dish, demonstrating the comparative antibacterial activity of compound 6a compared to antibiotic Amoxicillin against gram negative bacterial pathogen E. coli.
FIG. 5B is a photograph of a petri dish, demonstrating the comparative antibacterial activity of compound 6a compared to antibiotic Amoxicillin against gram negative bacterial pathogen S. typhi.
Figure 5C:
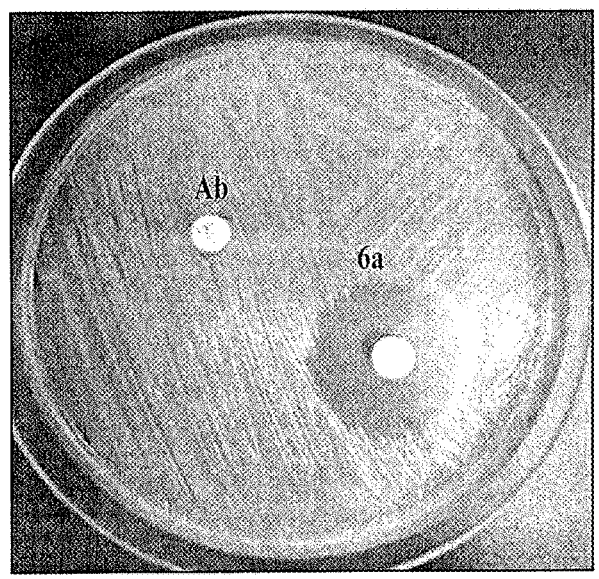
FIG. 5C is a photograph of a petri dish, demonstrating the comparative antibacterial activity of compound 6a compared to antibiotic Amoxicillin against gram negative bacterial pathogen P. aeruginosa.

A mechanism proposed to rationalize the formation of the cycloadduct 6 is summarized in FIG. 3A-3C. The effect of the ionic liquid catalysis is likely to be twofold. Besides solvent effects due to the dissolving power of this polar medium, the formation of N-heterocyclic carbene complexes may be due to active participation of the ionic liquid. The hydrogen atom of [bmim]$^+$, being electron-deficient, forms a hydrogen bond between the imidazole ring hydrogen atom of [bmim]$^+$ and the carbonyl group of isatin, enabling the attack of the lone pair on the thiazolidinecarboxylic acid on isatin, and the subsequent dehydration to produce azomethine ylide 7. See FIG. 3A. The hydrogen atom of [bmim]$^+$ also forms a hydrogen bond with the carbonyl group of dipolarophile 3, providing easy addition of the azomethine ylide to the more electron deficient β-carbon to afford the cycloadduct 6. See FIG. 3B.

These reactions apparently are (i) chemoselective as the azomethine ylide adds only to one of the C=C and not to C=O, and (ii) regioselective as the electron rich carbon of the dipole adds to the β carbon of the α,β-unsaturated ketone 3, affording the spirooxindole-pyrrolothiazole heterocyclic hybrid 6. The other regio isomer 8, which theoretically could be formed by the addition of electron rich carbon of the dipole to the α carbon of 3 (See FIG. 3C), apparently is not formed, even in traces.

Compounds 6a and 6b were tested for their antimicrobial activity against both gram positive and gram negative drug-resistant bacteria. Minimum inhibitory concentration (MIC) and minimum bactericidal concentration (MBC) values for compounds 6a and 6b, as compared with a reference antibacterial drug (ampicillin), for *Escherichia coli* (EC), *Pseudomonas aeruginosa* (PS), *Salmonella typhi* (ST), *Staphylococcus aureus* (SA), and *Staphylococcus epidermis* (SE) are reported in Tables 2A and 2B.

TABLE 2A

Antibacterial Testing Against *E. coli* and *P. aeruginosa*

| Compound | EC | | PS | |
|---|---|---|---|---|
| (μg/ml) | MIC | MBC | MIC | MBC |
| 6a | 14.62 | 29.25 | 29.25 | 58.55 |
| 6b | 29.25 | 58.55 | 58.55 | 117.15 |
| Ampicillin | 3.9 | 7.81 | — | — |

EC: *Escherichia coli*
PS: *Pseudomonas aeruginosa*

TABLE 2B

Antibacterial Testing Against *S. typhi, S. aureus* and *S. epidermis*

| Compound | ST | | SA | | SE | |
|---|---|---|---|---|---|---|
| (μg/ml) | MIC | MBC | MIC | MBC | MIC | MBC |
| 6a | 29.25 | 58.55 | 29.25 | 58.55 | 14.62 | 29.25 |
| 6b | 58.55 | 117.15 | 68.55 | 117.15 | 29.25 | 58.55 |
| Ampicillin | — | — | — | — | 3.9 | 7.81 |

ST: *Salmonella typhi*
SA: *Staphylococcus aureus*
SE: *Staphylococcus epidermis*

According to the MIC and MBC results, compound 6a showed potent activity against both control and drug-resistant strains at lower concentrations than compound 6b. The control strains of E. coli and S. epidermis exhibit the lowest MIC 14.62 µg ml$^{-1}$ and MBC 29.25 µg ml$^1$. The drug-resistant bacteria (PS, ST, and SA) produce virulence factors and regulate their metabolisms by sensing extra cellular signals in order to adapt to various environmental conditions. Compound 6a demonstrated MIC values of 29.25 µg ml$^{-1}$ and MBC values of 58.55 µg ml$^{-1}$ for these three bacterial strains, while compound 6b demonstrated MIC and MBC values for the drug resistance strains of MIC 58.55 µg ml$^{-1}$ and MBC 117.15 µg ml$^1$.

The qualitative screenings of antimicrobial activity were measured by plating in petri dishes to determine the formation of zones of inhibition for bacterial pathogens tested against compounds 6a, 6b and the standard antibiotic ampicillin. These results are summarized in in Table 3, while photographs of the petri dish results for compound 6a and the control ampicillin are set forth at FIGS. 4A, 4B, and 5A-C.

From Table 3, it is clear that compound 6a demonstrates the greatest activity against both drug resistant gram positive and gram negative bacterial pathogens.

TABLE 3

Antimicrobial activity (Zone of inhibition: diameter in mm)

| Compound | EC | PS | ST | SA | SE |
|---|---|---|---|---|---|
| 6a (60 µg/disc) | 27.3 ± 1.08 | 19.3 ± 0.81 | 22.3 ± 1.47 | 26.3 ± 0.81 | 31.3 ± 1.08 |
| 6b (120 µg/disc) | 18.6 ± 1.47 | 16.3 ± 1.63 | 16.3 ± 1.08 | 17.6 ± 1.47 | 19.3 ± 0.81 |
| Ampicillin (25 µg/disc) | 22.3 ± 1.77 | R | R | R (<13 | 23.3 ± 0.40 |

EC: *Escherichia coli*
PS: *Pseudomonas aeruginosa*
ST: *Salmonella typhi*
SA: *Staphylococcus aureus*
SE: *Staphylococcus epidermis*
R: Resistant The maximum zone of inhibition for compound 6a was observed against control strains of S. epidermis: 31.3±1.08 mm (see FIG. 4A) and E. coli: 27.3±1.08 mm (see FIG. 5A), followed by drug resistant S. aureus: 26.3±0.81 mm (see FIG. 4B); S. typhi: 22.3±1.47 mm (see FIG. 5B) and P. aeruginosa: 19.3±0.81 mm (see FIG. 5C).

Figures 6A, 6B:
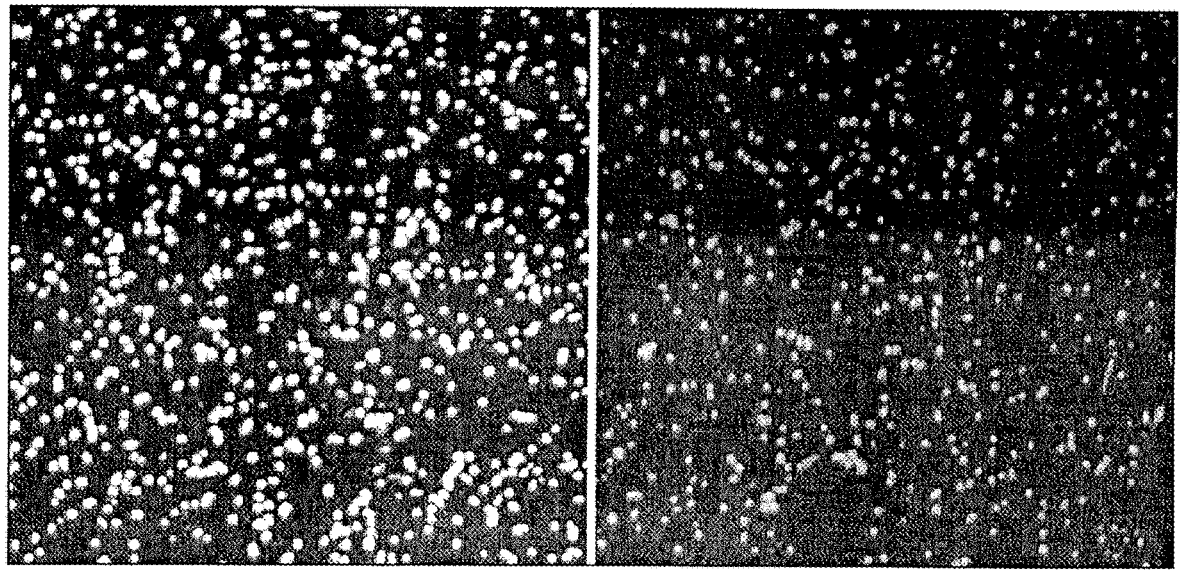
FIG. 6A is a micrograph from a live/dead bacterial double staining assay, showing untreated gram positive S. aureus.
FIG. 6B is a micrograph from a live/dead bacterial double staining assay, showing S. aureus after treatment with compound 6a, particularly dented, blistered and damaged cell walls in the bacteria.
Figures 6C, 6D:
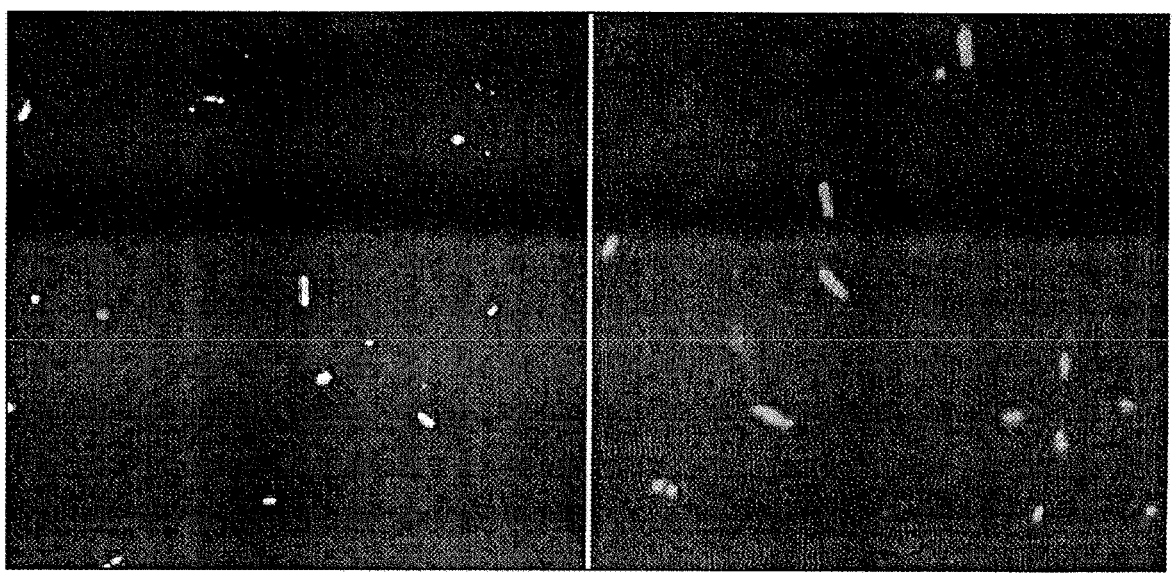
FIG. 6C is a micrograph from a live/dead bacterial double staining assay, showing untreated gram negative P. aeruginosa.
FIG. 6D is a micrograph from a live/dead bacterial double staining assay, showing P. aeruginosa after treatment with compound 6a, particularly dented, blistered and damaged cell walls in the bacteria.

The acridine orange (AO) and ethidium bromide (EB) double staining method was used to analyse the Live/dead bacterial cells for untreated and compound 6a-treated S. aureus and P. aeruginosa cells. Both sets of cells, treated and untreated for each of the two bacteria, were stained with AO/EB for 15 minutes. The unbound dyes were removed by rinsing the cells twice with phosphate buffer saline (PBS). 10 µl samples of each were then placed on a glass slide with coverslip, and observed using a ZEISS inverted florescent microscope. The untreated gram positive (FIG. 6A) and gram negative (FIG. 6C) bacterial cells appeared green due to the presence of healthy, viable cells with intact/undamaged cell membranes and uniform chromatin. In contrast, the compound 6a-treated cells (treated gram positive in FIG. 6B, and treated gram negative in 6D) appeared red due to the resulting dents, blisters and damaged cell walls on bacterial cells, providing entry for the EB dye. Thus, the AO/EB double staining confirms the bactericidal action of compound 6a through cell wall and cell membrane damage.

Figures 7A, 7B:
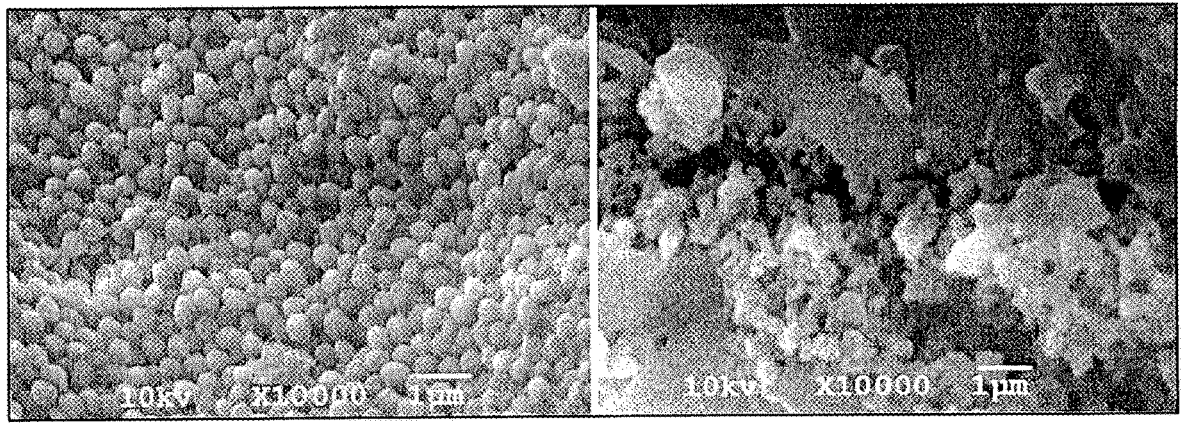
FIG. 7A is a SEM micrograph of untreated, drug-resistant S. aureus.
FIG. 7B is a SEM micrograph of drug-resistant S. aureus, treated with compound 6a and demonstrating dents, blisters, lysed cells, and cell debris.
Figures 7C, 7D:
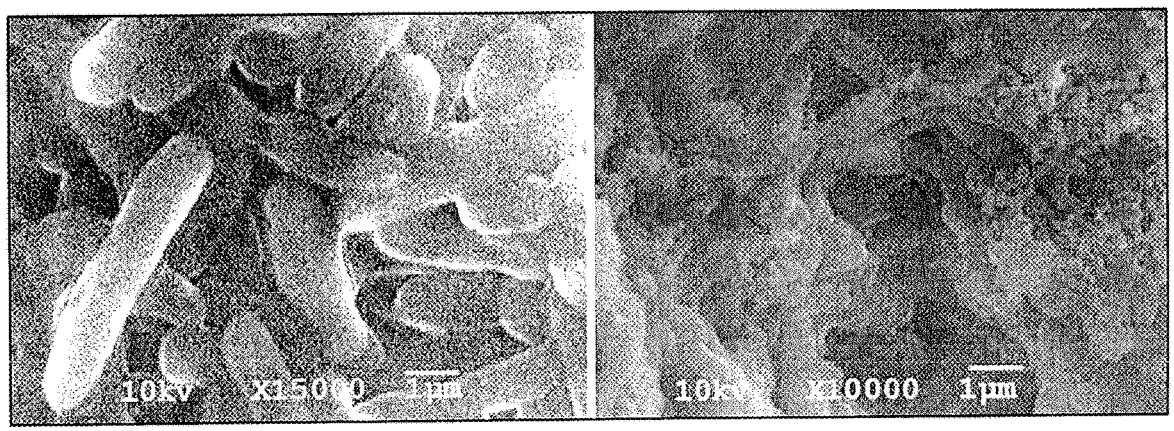
FIG. 7C is a SEM micrograph of untreated, drug-resistant P. aeruginosa.
FIG. 7D is a SEM micrograph of drug-resistant P. aeruginosa, treated with compound 6a and demonstrating dents, blisters, lysed cells, and cell debris.

The untreated and treated drug resistant S. aureus and P. aeruginosa bacterial cell morphology were evaluated by SEM analysis in order to assess the possible mechanisms of compound 6a. The control samples of untreated S. aureus (FIG. 7A) and P. aeruginosa (FIG. 7C) cells look clear and undamaged. Treatment with the compound 6a caused multiple dents and blisters, nuemerous lysed cells, and cell debris in both bacterial cells, as reflected in FIG. 7B for treated S. aureus, and in FIG. 7D for treated P. aeruginosa. The compound 6a appears to target the bacterial cellwall because the drug resistance of the tested bacteria is associated with the presence of an outer membrane, which hinders access to the inner membrane.

Figure 8A:
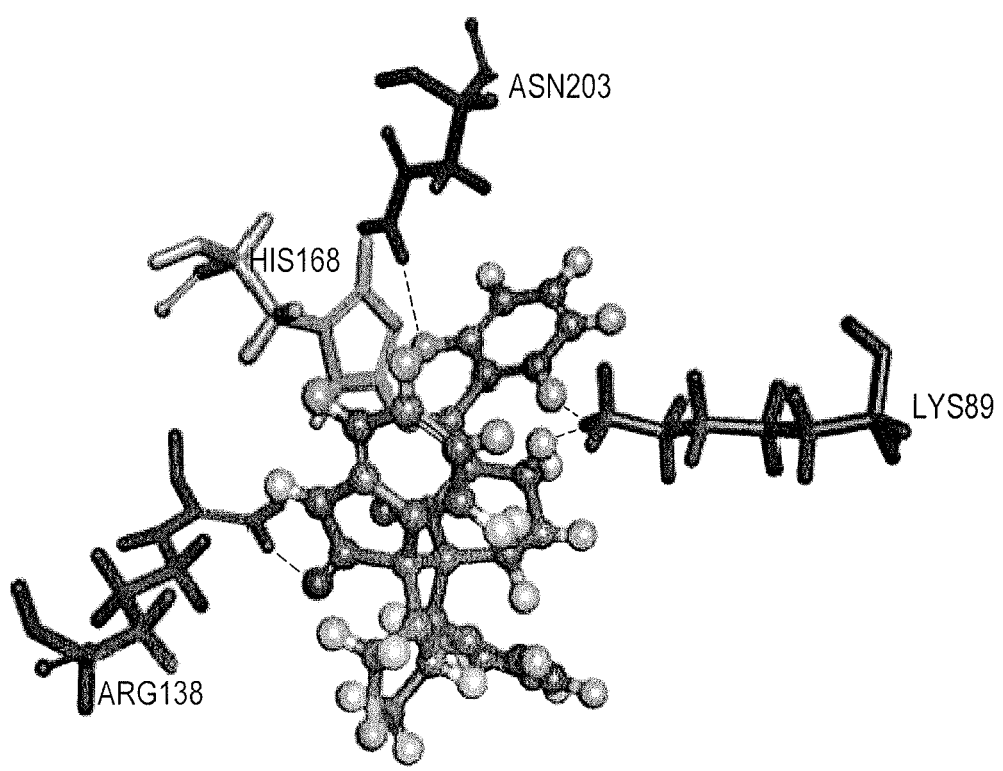
FIG. 8A is a molecular docking study image showing the docking complex of compound 6a with 4A3Q protein binding pockets.

The docking of compound 6a with binding pockets in proteins (enzymes) that are involved in bacterial cell wall synthesis were considered using the Discovery Studio software (DS 3.5) LibDock. D-Alanine (D-Ala) is an essential precursor for the synthesis of peptidoglycan in the bacterial cell wall of both gram positive and gram negative bacteria. Alanine racemase (Alr) is a unique enzyme involved in the survival of numerous bacteria through the racemization process of D-Ala. The inhibition of Alr results in growth arrest and cell lysis. In the docking analysis, the carbonyl functional group of compound 6a appears to interact with LYS89 and ARG138 complexes, demonstrating a binding energy of −100.237 kcal/mol and a LibDock score 53.06. See FIG. 8A.

Figure 8B:
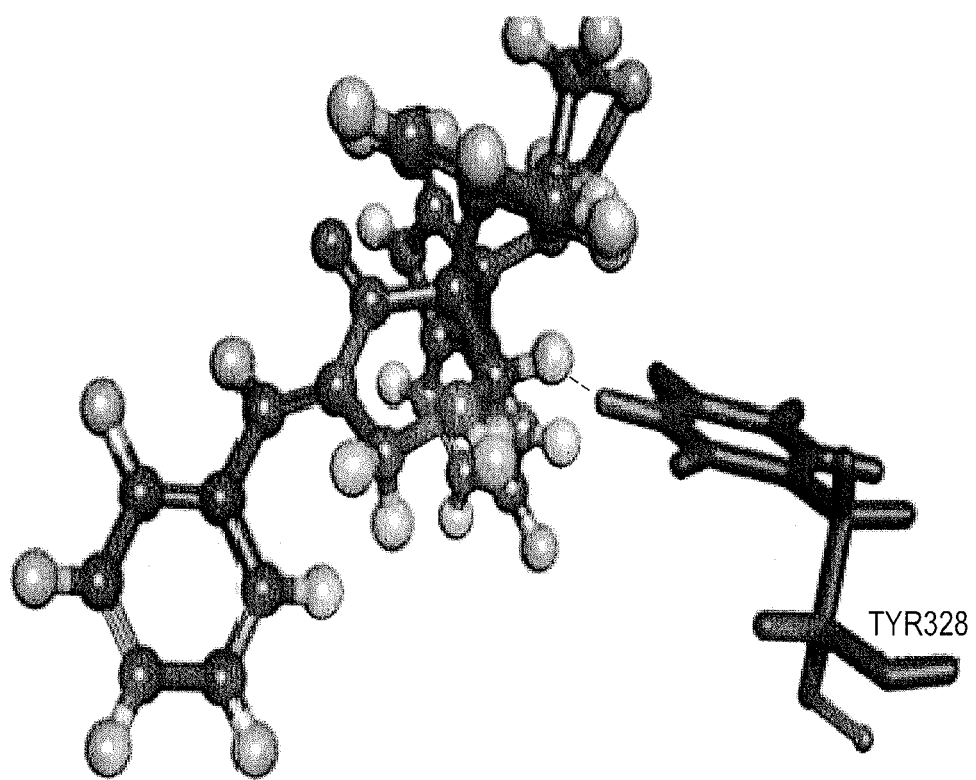
FIG. 8B is a molecular docking study image showing the docking complex of compound 6a with 4KQO protein binding pockets.

The interaction between compound 6a and the penicillin binding protein (PBP-4KQO) occurs in side chain residue TRY328. See FIG. 8B. The resulting binding energy was −115.817 kcal/mol, and the LibDock score was 97.05. The penicillin binding protein (PBP) polymerizes and modifies the peptidoglycan via crosslinking with peptide chains. Inhibitors of PBP can cause an alteration in the architecture of cell morphology via unlinking peptidoglycans.

Figure 8C:
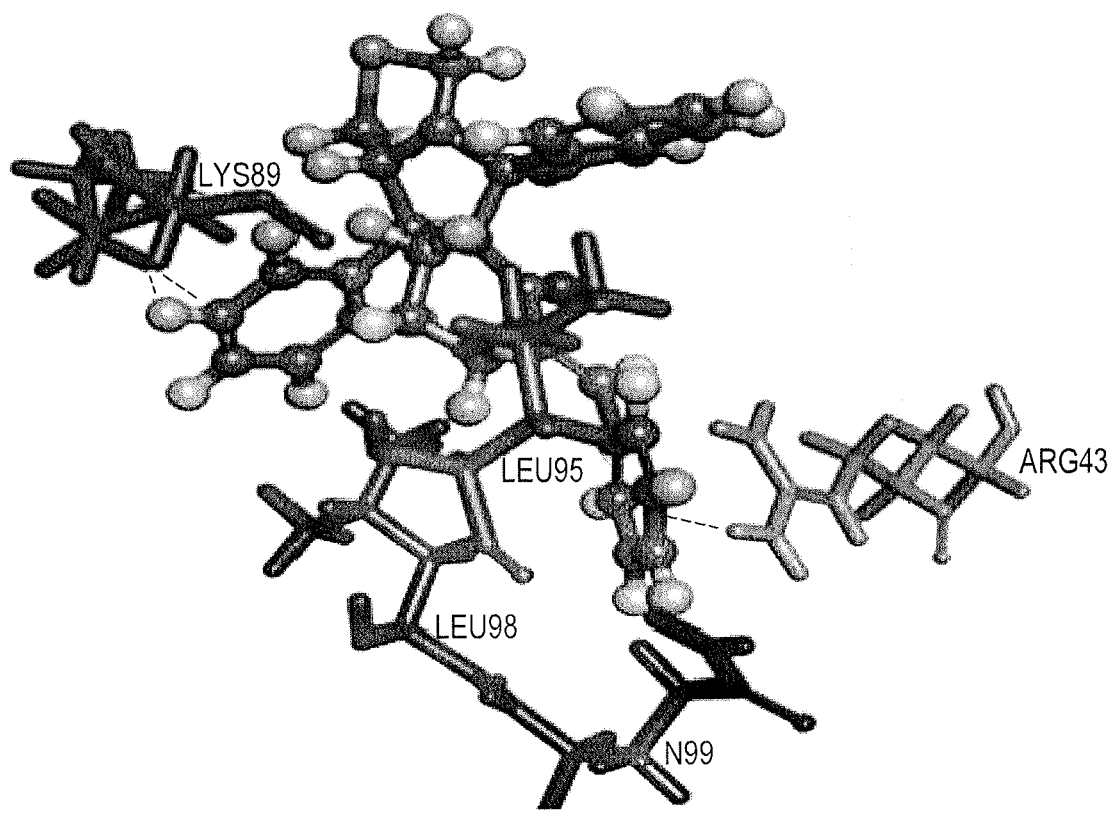
FIG. 8C is a molecular docking study image showing the docking complex of compound 6a with 5K9A protein binding pockets.

The highest binding affinity of compound 6a was found in connection with sortase protein (5K9A) residues ARG 43, LYS89, LEU95, LEU98 and GLN99 on the main chain (see FIG. 8C). This provided the most hydrogen bonding with the lowest binding energy −100.237, and a LibDock score of 67.87. The sortase enzyme decorates the bacterial surface with a diverse array of protein, and contributing to the virulence factor, adhesion to host tissue, host cell entry, and evasion, and effectively suppresses the host immune response. These results are summarized in Table 4.

TABLE 4

Ligand and protein binding pockets docking complex: binding energy (kcal/mol) and LipDock score

| Ligand | Protein | Residues | Absolute energy (kcal/mol) | Libdock score | H-bond | Length (A°) |
|---|---|---|---|---|---|---|
| 6a | 4A3Q | LYS38 | −100.237 | 53.06 | 1 | 2.47 |
|  |  | ARG138 |  |  | 2 | 1.61 |
|  |  | HIS168 |  |  | 1 | 2.24 |
|  |  | ASN203 |  |  | 2 | 1.121 |
|  | 4KQO | TRY328 | −115.817 | 97.05 | 1 | 1.124 |
|  | 5K9A | ARG 43 | −100.237 | 67.87 | 1 | 2.49 |
|  |  | LYS89 |  |  | 3 | 2.26 |
|  |  | LEU95 |  |  | 3 | 1.61 |
|  |  | LEU98 |  |  | 2 | 1.48 |
|  |  | GLN99 |  |  | 1 | 1.23 |

The sortase inhibition alters the cell wall sorting signal, resulting in translocation of amino proteins that are located on the cell surface. The inhibition activity of Alr and sortase supports the morphological changes, and thus multiple dents, blisters, and lysed and dead cells result, as reflected in the SEM images. Compound 6a significantly interacts with the residues in binding pockets of Alr, PBP and sortase proteins, as well as hydrogen bonding that otherwise stabilizes the docking complex. This may explain the broad spectrum activity against both gram positive and gram negative drug resistant bacteria.

Different physicochemical properties of compound 6a were calculated and presented in Table 5. Absorption, Distribution, Metabolism, Excretion, and Toxicity (ADMET) prediction results confirm the potent drug-like properties of 6a.

TABLE 5

In silico physico chemical properties of compound 6a

| S.No. | ADMET properties | Predictions |
| --- | --- | --- |
| 1 | H acceptors - 5 | Potent drug |
| 2 | H donors - 2 | |
| 3 | Rotatable bonds - 2 | Good bioavailability |
| 4 | Total energy (VAMP) - −6,607.43 | |
| 5 | Heat formation (VAMP) - 20.0684 | |
| 6 | HOMO eigenvalue - −8.5939 | |
| 7 | LUMO eigenvalue - −0.339593 | |
| 8 | Aqueous solubility level - 1 | |

The therapeutic action of drug-like compounds can be influenced by physiochemical properties (Table 5) that determine the drug delivery. Drugs with fewer hydrogen bond donor, acceptor and rotatable bonds are ideal for the administration of oral and injectable forms. Absorption is process of movement of drug in to systemic circulation from extravascular sites. The absorption quality of compound 6a was predicted in table 6.

TABLE 6

In silico absorption quality of compound 6a

| S. No. | ADMET properties | Predictions |
| --- | --- | --- |
| 1 | Aqueous solubility level - 1 | Moderate |
| 2 | Blood Brain Barrier(BBB) level - 1 | High |
| 3 | CYP2D6 level - 0 | Non inhibitor |
| 4 | Hepatotoxicity - −1.18089 | Mild |
| 5 | Plasma Protein Binding (PPB) level - 4 | ≥95% binding |
| 6 | Absorption level - 0 | Good absorption |
| 7 | APlog98 - 4.209 | Optimum cell permeability |
| 8 | PSA 2D - 63.574 | |

Compound 6a showed good absorption, optimum cell permeability PSA (2D—63.574) and AP (log 98—4.209), mild hepatotoxicity and non-inhibitors of CYP2D6. For compounds or drugs in the circulatory system, the blood brain barrier (BBB) acts as a physical barrier that stops the substances from traveling easily into the central nerve system (CNS). The In-silico results of BBB showed high level permeability expressed as log ($C_{brain}/C_{blood}$). The pharmacodynamics behavior of compound 6a was determined by Plasma Protein Binding (PPB). Compound 6a was measured and predicted ≥95% binding efficiency on PPB.

The in-silico carcinogenicity and toxicity assessment showed the potent drug likeliness of compound 6a, as reflected in Table 7. These prediction results revealed that compound 6a has no clinical adverse effects on rodent carcinogenicity, ICH genetic toxicity, reproductive and developmental toxicity assay.

TABLE 7

In silico Carcinogenicity and toxicity assessment of 6a

| S.No | ADMET properties | Predictions |
| --- | --- | --- |
| 1 | Ames Mutagenicity(Probability) - 0.253 | Non mutagen |
| 2 | Rodent carcinogenicity NTP (Probability) - 0.394 | |
| 3 | Rodent carcinogenicity FDA(Probability) - 0.199 | |
| 4 | Carcinogenic potency TD50 - 1.718 g/kg of body weight | All properties and OPS components are within expected ranges |
| 5 | RAT oral LD50 - 0.189 g/kg of body weight | |
| 6 | Rat maximum tolerated dose feed 0.0362 g/kg of body weight | |
| 7 | Rat chronic lowest observed adverse effect level (LOAEL) - 0.00759 g/kg of body weight | |
| 8 | Skin irritancy (Probability) - 0.597 | Non irritant |
| 9 | Ocular irritancy (Probability) - 0.822 | Mild |
| 10 | Aerobic biodegradability (Probability) - 0.400 | Non degradable |
| 11 | Fathead minnow LC50 - 0.00168 g/L | Within expected ranges |
| 12 | Daphnia magna EC50 - 0.0453mg/L | |

In the data that follows, melting points were taken using open capillary tubes, and are uncorrected. $^1$H and $^{13}$C NMR spectra were recorded on a Bruker 300 MHz instrument in $CDCl_3$ using TMS as internal standard. Standard Bruker software was used throughout. Chemical shifts are given in parts per million (δ-scale) and the coupling constants are given in Hertz. IR spectra were recorded on a Perkin Elmer system 2000 FT IR instrument (KBr). Elemental analyses were performed on a Perkin Elmer 2400 Series II Elemental CHNS analyzer. Column chromatography was performed on silica gel using petroleum ether-ethyl acetate (3:2v/v) as eluent.

Example 1

Synthesis of Compounds 6a and 6b

An equimolar mixture of 3,5-bis(4/2-fluorobenzylidene) piperidin-4-ones (3), isatin (4), and thioproline (5) in 200 mg of [bmim]Br was irradiated in a CEM microwave synthesizer at 100° C. for 10-15 min. After completion of the reaction (as ascertained by TLC), EtOAc (10 mL) was added and the reaction mixture was stirred for 15 min. The EtOAc layer was separated, washed with water (100 mL), dried over anhydrous $Na_2SO_4$ and evaporated. The product was obtained in excellent yield, and was purified by column chromatography techniques using petroleum ether-ethyl acetate (3:2v/v) as eluent. After extraction of the product, the ionic liquid ([bmim]Br) was completely dried under reduced pressure and reused for subsequent reactions.

Example 2

Characterization of Compound 6a

The test results for characterization of spiro[5.3″]-oxindole-spiro-[6.2′]-6′-(4-fluorophenylmethylidene)tetrahydro-4′(1H)-pyridinone-7-(4-fluorophenyl)tetrahydro-1H-pyrrolo [1,2-c][1,3] thiazole (compound 6a) were as follows. Light brown solid; Yield=90%; mp 252-254° C.; IR (KBr) $\upsilon_{max}$ 3335, 1712, 1617 $cm^{-1}$; $^1$H NMR (300 MHz, $CDCl_3$): $\delta_H$ 2.33 (d, J=−12.9 Hz, 1H, H-2′a), 2.82 (dd, J=10.2, 6.0 Hz, 1H, H-1a), 3.03 (dd, J=10.2, 5.7 Hz, 1H, H-1b), 3.42 (dd, J=14.4, 2.1 Hz, 1H, H-6′a), 3.51 (d, J=7.2 Hz, 1H, H-3a), 3.67 (d, J=14.4 Hz, 1H, H-6'b), 3.72 (d, J=7.2 Hz, 1H, H-3b), 3.93 (d, J=12.6 Hz, 1H, H-2'b), 4.44 (d, J=10.2 Hz, 1H, H-7), 4.62-4.69 (m, 1H, H-7a), 6.52 (s, 1H, H-8), 6.67 (d, J=8.1 Hz, 2H, ArH), 6.85-7.41 (m, 10H, ArH), 8.25 (s, 1H, NH); $^{13}$C NMR (75 MHz, CDCl$_3$): $\delta_C$ 34.5, 48.2, 49.1, 49.6, 50.1, 69.8, 72.4, 73.5, 109.7, 115.7, 116.0, 122.5, 126.0, 129.1, 129.8, 131.5, 132.1, 132.6, 132.8, 135.3, 135.6, 141.5, 159.8, 162.7, 179.1, 198.7. Anal. calcd. for $C_{30}H_{25}F_2N_3O_2S$: C, 68.04; H, 4.76; N, 7.93. Found: C, 68.27; H, 4.58; N, 7.81%.

Example 3

Characterization of Compound 6b

The test results for characterization of spiro[5.3"]-oxindole-spiro-[6.2']-6'-(2-fluorophenylmethylidene)tetrahydro-4'(1H)-pyridinone-7-(2-fluorophenyl)tetrahydro-1H-pyrrolo[1,2-c][1,3] thiazole (compound 6b) were as follows. Light brown solid; Yield=87%; mp 245-247° C.; IR (KBr) $\upsilon_{max}$ 3332, 1708, 1619 cm$^{-1}$; $^1$H NMR (300 MHz, CDCl$_3$): $\delta_H$ 2.37 (d, J=13.2 Hz, 1H, H-2'a), 2.84-2.89 (m, 1H, H-1a), 3.01 (dd, J=9.6, 5.7 Hz, 1H, H-1b), 3.42-3.52 (m, 2H, H-6'a and H-3a), 3.59-3.66 (m, 2H, H-6'b and H-3b), 3.84 (d, J=13.2 Hz, 1H, H-2'b), 4.52-4.60 (m, 1H, H-7a), 4.69 (d, J=9.3 Hz, 1H, H-7), 6.69 (d, J=7.8 Hz, 1H, ArH), 6.84-7.31 (m, 11H, ArH), 7.61-7.66 (m, 1H, ArH), 8.22 (s, 1H, NH); $^{13}$C NMR (75 MHz, CDCl$_3$): $\delta_C$ 34.1, 44.2, 48.4, 48.7, 50.0, 69.4, 71.1, 73.1, 109.8, 115.9, 116.2, 122.8, 123.3, 123.5, 124.2, 124.6, 125.7, 129.1, 129.3, 129.8, 130.8, 131.0, 131.6, 135.4, 136.7, 141.5, 159.6, 162.9, 178.4, 197.5. Anal. calcd. for $C_{30}H_{25}F_2N_3O_2S$: C, 68.04; H, 4.76; N, 7.93. Found: C, 68.22; H, 4.91; N, 7.76%.

The quantitative and qualitative screening of anti-bacterial activity of compounds 6a and 6b was conducted, the results being described above. Quantitative screening was determined by minimal inhibitory concentration (MIC) and minimal bactericidal concentration (MBC), while qualitative screening was accomplished by disc diffusion method. *E. coli* (ATCC—25922) and *S. epidermis* (ATCC 12228) were used as standard strains, and drug-resistant pathogens *P. aeruginosa*, *S. typhi*, and *S. aureus* were used to screen the antimicrobial activity. Gram negative bacteria were maintained on nutrient broth (NB)/agar plates (NA) and gram positive bacteria were maintained on trypticase soy broth (TSB)/agar plates (TSA). The compounds 6a and 6b concentration range was prepared by two-fold dilution in a sterile broth from the stock, using a microtiter 96 well plate method. Twelve dilutions of each compound, ranging from 7500 to 3.65 µg/ml, were tested, and Ampicillin was used as a positive control agent (with a range of 500 to 0.24 µg/ml).

Qualitative screening of synthesized compounds was analyzed using sterile disc impregnated with compounds at the concentration of 60 µg/disc (for compound 6a) and 120 g/disc (for compound 6b), and then incubated at 40° C. for 30 min to remove solvent. The mid log bacterial inoculum was speeded on NA/TSA and the loaded disc was placed on agar plates and incubated at 37° C. for 24h. After this period, the inhibitions produced by the compounds around the disc were measured using antibiotic zone scale (Hi-Media, Mumbai, India) and zone of inhibitions were measured in mm.

Fluorescent dye stock solution was prepared by dissolving equal quantities of acridine orange (AO) and ethidium bromide (EB)—10 mg each—in 10 ml of PBS. The working solution was prepared by diluting 200 µl of stock solution into 10 ml of PBS. The 1 ml sample of mid log bacterial suspension was harvested by centrifugation at 3000 rpm for 10 minutes. The pellet was collected and washed twice with PBS, and then treated with compound 6a at MIC and incubated for 4 hours. The unbounded dye was removed by washing with PBS, and 10 µl of sample was placed on a glass slide and observed under a ZEISS fluorescent inverted microscope. The controls were processed without compound 6a treatment.

The morphological changes on 6a-treated bacterial cells were investigated by scanning electron microscopic (SEM) analysis. The 1 ml sample of mid log bacterial suspension was harvested by centrifugation at 3000 rpm for 10 min. The pellet was collected and washed twice with PBS and treated with compound 6a at MIC and incubated for 4h. The cell suspension (10 µl) was dropped on a treated glass slide, and fixed with 2.5% glutaraldehyde. Then the fixed cells were dehydrated with sequential treatment of 10%, 30%, 50%, 70%, 90% and 100% ethanol for 10 minutes. The samples were lyophilized with a critical point dryer, sputter-coated with platinum, and then imaged on a JEOL JSM 5800 SEM (JEOL, Tokyo, Japan).

The enzymes that are involved in bacterial cell wall synthesis were selected as receptors for the docking analysis. The selected receptors are Alanine racemase (PDB-4A3Q), penicillin binding protein (PDB ID-4KQO), and Sortase (PDB ID-5K9A).

Crystal structures of these proteins were retrieved from the protein data bank (rcsb.org/pdb). The receptors and ligand molecules were prepared, and the molecular docking calculations were performed using LibDock protocol under receptor-ligand interaction section in Discovery Studio (DS) 3.5 (Accelrys, USA). The docking was carried out as described elsewhere. The results suggested the target compound 6a acts as a protein inhibitor.

The metabolisms, toxicity and pharmacokinetics properties of compound 6a were analyzed by in-silico computational methods. This in silico prediction revealed how compound 6a is expected to behave in the human body. Such testing is an alternative to in vivo testing, and can be confirmed by the drug properties exhibited by the target compounds.

The drug-like properties of compound 6a were measured quantitatively using Discovery Studio 3.5 (Accelrys) under "toxicity prediction—komputer assisted technology" (TOPKAT) programme.

It is to be understood that the spirooxindole-pyrrolothiazole heterocyclic hybrids are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A spirooxindole-pyrrolothiazole heterocyclic hybrid of the formula:

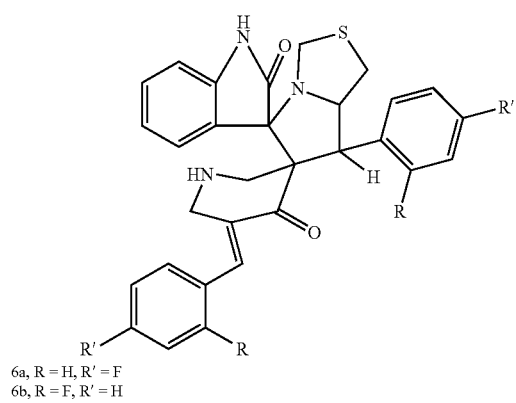

6a, R = H, R' = F
6b, R = F, R' = H wherein R is hydrogen and R' is fluorine, or R is fluorine and R' is hydrogen.

2. The spirooxindole-pyrrolothiazole heterocyclic hybrid according to claim 1, wherein R is hydrogen and R' is fluorine.

3. The spirooxindole-pyrrolothiazole heterocyclic hybrid according to claim 1, wherein R is fluorine and R' is hydrogen.

4. A method of making a spirooxindole-pyrrolothiazole heterocyclic hybrid of the formula,

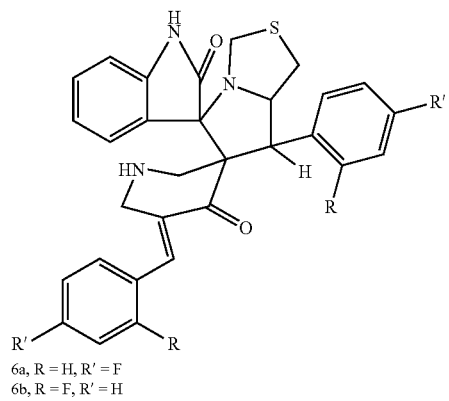

6a, R = H, R' = F
6b, R = F, R' = H wherein R is hydrogen and R' is fluorine, or R is fluorine and R' is hydrogen,
comprising the step of reacting a mixture of a 3,5-bis(fluorobenzylidene)piperidin-4-one aldehyde with isatin and 4-thiazolidinecarboxylic acid.

5. The method of making a spirooxindole-pyrrolothiazole heterocyclic hybrid according to claim 4, wherein the reacting step further comprises reacting the mixture in methanol under reflux conditions for one hour.

6. The method of making a spirooxindole-pyrrolothiazole heterocyclic hybrid according to claim 4, wherein the reacting step further comprises reacting the mixture in dioxane under reflux conditions for one hour.

7. The method of making a spirooxindole-pyrrolothiazole heterocyclic hybrid according to claim 4, wherein the reacting step further comprises reacting the mixture in methanol and dioxane under reflux conditions for one hour.

8. The method of making a spirooxindole-pyrrolothiazole heterocyclic hybrid according to claim 4, wherein the reacting step further comprises reacting the mixture in ethanol under reflux conditions for one hour.

9. The method of making a spirooxindole-pyrrolothiazole heterocyclic hybrid according to claim 4, wherein the reacting step further comprises reacting the mixture in isopropanol under reflux conditions for one hour.

10. The method of making a spirooxindole-pyrrolothiazole heterocyclic hybrid according to claim 4, wherein the reacting step further comprises reacting the mixture in 1-butyl-3-methylimidazolium bromide at 100° C. for thirty minutes.

11. The method of making a spirooxindole-pyrrolothiazole heterocyclic hybrid according to claim 4, wherein the reacting step further comprises reacting the mixture in 1-butyl-3-methylimidazolium bromide at 100° C. under microwave irradiation.

12. The method of making a spirooxindole-pyrrolothiazole heterocyclic hybrid according to claim 4, wherein the reacting step further comprises reacting the mixture in 1-butyl-3-methylimidazolium bromide at 100° C. under microwave irradiation for between ten and fifteen minutes.

13. The method of making a spirooxindole-pyrrolothiazole heterocyclic hybrid according to claim 12, further comprising the step of extracting the spirooxindole-pyrrolothiazole heterocyclic hybrid from the mixture in ethyl acetate.

14. The method of making a spirooxindole-pyrrolothiazole heterocyclic hybrid according to claim 12, further comprising the step of drying the 1-butyl-3-methylimidazolium bromide under reduced pressure for reuse.

15. The method of making a spirooxindole-pyrrolothiazole heterocyclic hybrid according to claim 4, wherein the 3,5-bis(fluorobenzylidene)piperidin-4-one aldehyde is 3,5-bis(4-fluorobenzylidene)piperidin-4-one.

16. An antibacterial composition, comprising a spirooxindole-pyrrolothiazole heterocyclic hybrid antibacterial agent of the formula,

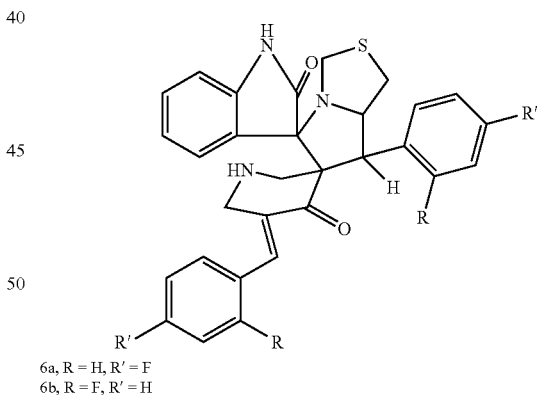

6a, R = H, R' = F
6b, R = F, R' = H wherein R is hydrogen and R' is fluorine, or
R is fluorine and R' is hydrogen, made according to the method of claim 15.

17. The method of making a spirooxindole-pyrrolothiazole heterocyclic hybrid according to claim 4, wherein the 3,5-bis(fluorobenzylidene)piperidin-4-one aldehyde is 3,5-bis(2-fluorobenzylidene)piperidin-4-one.

18. An antibacterial composition, comprising a spirooxindole-pyrrolothiazole heterocyclic hybrid antibacterial agent of the formula,

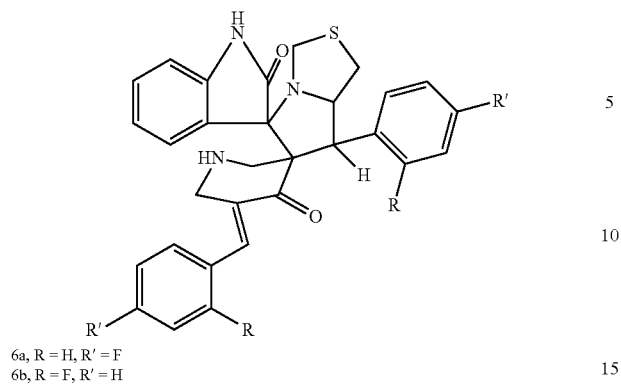
6a, R = H, R' = F
6b, R = F, R' = H
wherein R is hydrogen and R' is fluorine, or
R is fluorine and R' is hydrogen, made according to the method of claim 17.
* * * * *